United States Patent [19]

Kragten et al.

[11] Patent Number: 5,364,962
[45] Date of Patent: Nov. 15, 1994

[54] METHOD FOR PURIFICATION OF A BENZOIC ACID

[75] Inventors: Ubaldus F. Kragten, Beek; Miriam K. J. Frohn-Schlösser, Kerkrade, both of Netherlands

[73] Assignee: Stamicarbon B.V., Geleen, Netherlands

[21] Appl. No.: 974,663

[22] Filed: Nov. 12, 1992

Related U.S. Application Data

[63] Continuation of Ser. No. 683,818, Apr. 11, 1991, abandoned.

[30] Foreign Application Priority Data

Apr. 14, 1990 [NL] Netherlands ................. 9000891

[51] Int. Cl.⁵ .................................................. C07C 51/42
[52] U.S. Cl. ........................................................ 562/494
[58] Field of Search ........................................... 562/494

[56] References Cited

U.S. PATENT DOCUMENTS

| | | | |
|---|---|---|---|
| 3,078,303 | 3/1959 | Sweeney et al. | 260/525 |
| 4,092,353 | 5/1978 | Wolf | 562/494 |
| 4,227,017 | 5/1979 | Jongsma et al. | 562/494 |
| 4,323,702 | 4/1982 | Kawabata et al. | 562/494 |

FOREIGN PATENT DOCUMENTS

| | | | |
|---|---|---|---|
| 0347621 | 12/1989 | European Pat. Off. | |
| 0351627 | 1/1990 | European Pat. Off. | |
| 2636489 | 12/1977 | Germany | 562/494 |
| 57-118523 | 7/1982 | Japan | 562/494 |
| 958438 | 4/1961 | United Kingdom | |
| 2039278 | 8/1980 | United Kingdom | |
| 0925933 | 5/1982 | U.S.S.R. | 562/494 |

*Primary Examiner*—José G. Dees
*Assistant Examiner*—B. Frazier
*Attorney, Agent, or Firm*—Cushman Darby & Cushman

[57] ABSTRACT

The invention relates to a method for the purification of benzoic acid, which is obtainable through oxidation of the corresponding toluene derivative, by treating it with a —$NH_2$ or —NHR containing component in which R represents a carbon containing group, said component being applied to a support.

13 Claims, No Drawings

METHOD FOR PURIFICATION OF A BENZOIC ACID

This is a continuation of application Ser. No. 07/683,818, filed on Apr. 11, 1991, now abandoned.

The invention relates to a method for the purification of a benzoic acid, whether or not substituted, which is obtainable through oxidation of the corresponding toluene derivative, by treating the benzoic acid with a —$NH_2$ or —NHR containing component in which R represents a carbon containing group. The invention also relates to a method for the preparation of a benzoic acid salt.

Such a method for the purification of a benzoic acid is known from EP-A-163212. A benzoic acid obtained in the oxidation of a toluene is purified, i.e. impurities that interfere with the further processing and application of the benzoic acid are removed in a distillative treatment of the crude benzoic acid in the presence of aliphatic amines of the formula $HNR^1R^2$, $R^1$ being an H or a hydroxyalkyl or aminoalkyl residual group and $R^2$ being a hydroxyalkyl or aminoalkyl residual group, mentioned alkyl groups consisting of 1–6 carbon atoms. Salts derived from the amines may also be used. However, it has been found that the use of the described method leads to a product from which the impurities originally contained in the crude benzoic acid are at least partly removed but that the product is slightly, and undesirably, contaminated with N-containing compounds. These compounds are either the amines used or products derived therefrom, formed in the distillative treatment. This is even more the case when an excess of amine is used. Furthermore, there is a formation of undesired odours in the purified product. In addition, these N-containing compounds may cause problems in the further processing of the benzoic acid. A further disadvantage of the method described above is that the bottoms remaining after the treatment are contaminated with nitrogen-containing compounds foreign to the process and may therefore not be recirculated to the benzoic acid preparation section as such.

The invention provides a method that yields a purified benzoic acid that does not present the aforementioned drawbacks. This is achieved by using a purifying agent in which—and this characterizes the invention—the —$NH_2$ or —NHR containing component is applied to a support.

By applying the —$NH_2$ or —NHR containing component to a support a heterogeneous purifying agent is obtained that can easily be separated from the purified benzoic acid. It is also possible to regenerate the purifying agent after use and to make it suitable for re-use. The purifying agent according to the described state of the art, on the contrary, can usually be used once only. Because of this, the problems of the undesired contamination with N-containing compounds do not occur. Furthermore, it appears that the formation of odour is circumvented with using this process.

The use of an N-containing, basic component to purify a benzoic acid is based on the discovery that it is primarily acids or anhydrides derived therefrom that constitute the contaminations in a benzoic acid. The benzoic acid which is obtained through catalytic oxidation of toluene contains, for example, phthalic acid and phthalic anhydride as undesired contaminations.

It has thus been found that purifying agents that contain a primary (—$NH_2$) or secondary (—NHR) group, are very suitable for purifying such a benzoic acid. Tertiary amino groups are per se also capable of removing such impurities but their effectivity is very limited.

The heterogeneous purifying agent to be used for said purification must meet a number of requirements. One of the main requirements is that the agent is thermally and chemically stable in the benzoic acid to be treated. A man skilled in the art can easily find out, whether or not the amino group bearing heterogeneous purifying agent meets this requirement. In general, this means that when treating liquid benzoic acid it will have to be possible to use such an agent at temperatures of over 120° C., in particular at temperatures of 125°–180° C. In addition to the benzoic acid as such, it is also possible to use solutions of benzoic acid. One of the reasons for using solutions may be that the treatment temperature may be lowered (melting temperature vs. dissolution temperature). The corresponding toluene is a pre-eminently suitable solvent because it is already present in the oxidative preparation of the benzoic acid. Purifying agents that are partly dissolved by the reaction medium, i.e. the solvent or the benzoic acid under the process conditions to be applied are therefore not suitable. As "support" is therefore meant here, a for the process stable heterogeneous agent.

Of course, it is preferable to use a purifying agent that ensures that the contaminations to be removed are irreversibly retained and that the benzoic acid to be purified is not or only reversibly retained by the purifying agent in the purification.

As purifying agent use may be made of a weak-base ion exchanger. The support usually used for this purpose, which is provided with the required —$NH_2$ or NHR groups, consists of a polystyrene resin that is cross-linked with divinylbenzene. In such a method according to the present invention the purifying agent is used to bind the acids and anhydrides present to the amine groups via a reaction rather than to exchange ions. Organic carriers are described in—for example—Coordination Chemistry reviews 1984, 59, pp. 1–139.

Another very suitable support is silica. Such a material is available both in a natural form and in a synthetic form and can be provided with the desired —$NH_2$ or NHR groups via methods known per se. Other inorganic carriers consist for instance of silica-alumina mixtures.

As basic material for the method according to the invention use may be made of crude benzoic acid, which can be obtained through oxidation of the corresponding toluene. Here and below the term benzoic acid is understood to be compounds of the following structural formula:

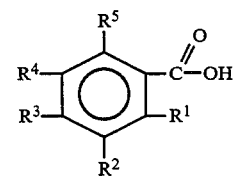

In the simplest case $R^1$–$R^5$ are hydrogen atoms. One or more of these hydrogen atoms may be substituted so that $R^2$–$R^5$ may be e.g. alkyl, cycloalkyl, aralkyl, hydroxyl or carboxyl groups or, for example, halogenides. Preferably, the method is used for unsubstituted benzoic acid ($R^1$–$R^5$ being hydrogen), which can be obtained through oxidation of unsubstituted toluene.

The purifying agent to be used must contain —$NH_2$ or —NHR groups, as indicated. When use is made of an —NHR group, R may be a $C_1$–$C_8$ alkyl, whether or not substituted, a cycloalkyl or an aryl group. A hydroxy or amino group, for example, may be present as a substituent.

The method according to the invention may be applied at any place in the process for the preparation of benzoic acid where there is a stream containing benzoic acid. For example, the purifying agent may be used in a stream of benzoic acid that comes from the distillative processing of crude benzoic acid, which may come from the oxidation of the corresponding toluene. The processing may be effected either in batch mode or in continuous mode, using either a slurry process or a fixed-bed process. Preferably, the purifying agent is used in a distillative purification step, which renders a separate treatment of the distillate superfluous. It is particularly preferred to apply this purification treatment directly before the actual destillation, for instance, in a fixed bed pre-column, because in that case the present method prevents exposure of the purifying agent to extremely high temperatures (such as those in the reboilers of distillation columns). This enhances the stability of the agent and prevents contamination of the benzoic acid with components of the purifying agent.

The residence time of the to be treated mixture is in general more than 5 minutes. Even within half an hour well purified benzoic acid was obtained. Depending on the to be purified mixture, impurities and the heterogeneous purifying agent, the residence time can be adjusted. Generally a residence time longer than 6 hr will not be applied. Preferably the to be purified liquid will be treated with the purifying agent during 10 min–3 hr.

According to the method, the purifying agent is loaded with contaminations, as a result of which it looses its purifying effect after some time. In such a situation the agent can be regenerated to remove the bound contaminations and render the purifying agent suitable for a next purification process, for which saponification with the aid of a hydroxide (solution) (in particular NaOH (sodium hydroxide)) or hydrolysis with the aid of an acid (solution) may be considered. Such regeneration takes place at room temperature or a slightly elevated temperature. A treatment at a temperature that corresponds to that used for the purification of the benzoic acid is also suitable.

The quality of the benzoic acid thus purified is such that the product may be used as a food additive or as a starting material in the pharmaceuticals industry. Not only the benzoic acid but also, and this also is a part of the invention, the salts obtainable therefrom meet high purity criteria (such as described in the British Pharmacopi requirement). Such salts can be obtained by reacting the purified benzoic acid in a manner known per se with an alkali or an alkaline-earth metal compound. This applies to the preparation of sodium benzoate in particular.

The invention will be illustrated with the following examples and comparative experiments, without introducing a limitation thereto.

COMPARATIVE EXPERIMENT A 100 grams of benzoic acid, contaminated with 0.3 wt. % phthalic acid and phthalic anhydride (PA) was treated in a Vigreux distillation column, at a pressure of 2000 Pa and a top temperature of 150° C. The distillation was carried out for 3 hours in the presence or absence of a soluble amino compound, after which the products obtained were chromatographically (HPLC) analysed to determine the phthalic acid and phthalic anhydride contents. The nitrogen content was also determined. The results obtained are shown in Table I.

TABLE I

| Exp. No. | Purifying agent | molar ratio*) | distillate PA wt. % | distillate N wt. % | residue N wt. % |
|---|---|---|---|---|---|
| A-1 | — | — | 0.27 | — | — |
| A-2 | $NH_3$ | 5.0 | 0.04 | 0.06 | 0.31 |
| A-3 | ethanolamine | 3.6 | <0.01 | 0.03 | 0.20 |

*)the ratio of the amount of purifying agent and the amount of PA.

EXAMPLE I 1.0 gram of weak-base ion exchanger (Merck II, Trade name 4766, particle size 0.3–0.9 mm) was added to 50 grams of melted benzoic acid containing 0.3 wt. % PA.

The treatment took place at a temperature of 130° C. for 1 hour. The PA and nitrogen contents were determined of the liquid thus obtained. The results are shown in Table II.

TABLE II

| Exp. | % water (1) | purified PA wt. % | benzoic acid N ppm |
|---|---|---|---|
| I-1 | 39 | <0.01 | <100 |
| I-2 | 3.2 (2) | <0.01 | <100 |
| I-3 | 13.6 (3) | <0.01 | <100 |

(1) water content of the fresh exchanger
(2) water content of the exchanger reduced through azeotropic distillation with the aid of toluene
(3) the same, only now through suppression with the aid of ethanol

EXAMPLE II

Streams of 140 and 64 grams/hour of benzoic acid containing 0.3 wt. % PA were passed through a double-walled column filled with 20 grams of dry exchanger (Merck II), at a temperature of 140° C.

Before the test the exchanger was dried for one night in a vacuum stove at 60° C. The streams obtained were analysed in the same way as above. The results are shown in Table III.

TABLE III

| Example | Residence time (min) | purified PA wt. % | benzoic acid N ppm |
|---|---|---|---|
| II-1 | 30 | <0.01 | <100 |
| II-2 | 65 | <0.01 | <100 |

EXAMPLE III

Example II was repeated using 100 grams/hour of benzoic acid that contained 0.13 wt. % PA. This was passed over the Merck II exchanger (27 grams). The benzoic acid obtained, which contained <0.01% PA and <100 ppm nitrogen, was used to prepare sodium benzoate. The sodium benzoate thus obtained met the British Pharmocopi requirement for sodium benzoate.

EXAMPLE IV

A purifying agent consisting of a silica support modified with N-3(trimethoxysilylpropyl)ethylenediamine (total base content 0.51 mgeq/gram) was prepared according to the procedure described in Inorg. Chim. Acta, 30(1978) pp. 51–58.

A benzoic acid containing 0.31 wt. % PA was treated at 140° C. with a 5-fold excess of this purification agent for 60 minutes. After this period the liquid contained <0.01% PA and <100 ppm nitrogen.

A test in which the benzoic acid was dissolved in toluene and a temperature of 90° C. was used yielded an analogous result.

The same result was obtained when a silica support, similarly modified with 3-aminopropyltrimethoxysilane or N-methyl-3-aminopropyltrimethoxysilane, was used as a purifying agent.

We claim:

1. Method for the purification of a benzoic acid obtained through oxidation of a corresponding toluene derivative comprising the steps of:
   treating the benzoic acid with a stable heterogeneous purifying agent, the stable heterogeneous purifying agent comprising a support having provided thereon —$NH_2$ or —NHR groups, wherein R is selected from the group consisting of an alkyl, a cycloalkyl, and an aryl group.

2. Method according to claim 1, wherein the stable heterogeneous purifying agent is a weak-base ion exchanger.

3. Method according to claim 1, wherein the benzoic acid is treated with the stable heterogeneous purifying agent during a distillation process step of the benzoic acid.

4. Method according to claim 1, wherein the benzoic acid is treated with the stable heterogeneous purifying agent directly before a distillation process step of the benzoic acid.

5. Method according to claim 1, wherein the benzoic acid is treated with the stable heterogeneous purifying agent at a temperature of 125°–180° C.

6. Method according to claim 1, wherein the support consists of silica.

7. Method according to claim 1, wherein the support consists of polystyrene resin that is cross-linked with divinylbenzene.

8. Method according to claim 1, wherein R is selected from the group consisting of a $C_1$–$C_8$ alkyl, a cycloalkyl and an aryl group.

9. Method according to claim 1, wherein the stable heterogeneous purifying agent is regenerated, after which the regenerated stable heterogeneous purifying agent can be reused in the method according to claim 1.

10. Method according to claim 1, wherein the support can be used at temperatures of over 120° C.

11. Method according to claim 9, wherein the stable heterogeneous purifying agent is regenerated by saponification with a solution comprising a hydroxide.

12. Method according to claim 9, wherein the stable heterogeneous purifying agent is regenerated by hydrolysis with a solution comprising an acid.

13. Method according to claim 1, wherein the residence time of the to be purified benzoic acid in the presence of the stable heterogeneous purifying agent is between 5 minutes and 6 hours.

* * * * *